(12) United States Patent
Shikhman et al.

(10) Patent No.: US 6,350,227 B1
(45) Date of Patent: Feb. 26, 2002

(54) AFTERLOADER APPARATUS

(75) Inventors: Oleg Shikhman, Fairfield; James Correia, Shelton, both of CT (US); Sam F. Liprie, Lake Charles, LA (US); Stansislaw Kostrzewski, Newton, CT (US)

(73) Assignee: Interventional Therapies, LLC, Westport, CT (US)

( * ) Notice: Subject to any disclaimer, the term of this patent is extended or adjusted under 35 U.S.C. 154(b) by 0 days.

(21) Appl. No.: 09/509,253

(22) PCT Filed: Sep. 23, 1998

(86) PCT No.: PCT/US98/19820

§ 371 Date: Jun. 12, 2000

§ 102(e) Date: Jun. 12, 2000

(87) PCT Pub. No.: WO99/15235

PCT Pub. Date: Apr. 1, 1999

Related U.S. Application Data

(60) Provisional application No. 60/059,602, filed on Sep. 23, 1997.

(51) Int. Cl.[7] .................................................. A61N 5/00
(52) U.S. Cl. .......................................................... 600/7
(58) Field of Search ........................................ 600/1–8

(56) References Cited

U.S. PATENT DOCUMENTS

| | | |
|---|---|---|
| 5,030,194 A | 7/1991 | Hooft |
| 5,092,834 A | 3/1992 | Bradshaw et al. |
| 5,103,395 A | 4/1992 | Spako et al. |
| 5,139,473 A | 8/1992 | Bradshaw et al. |
| 5,800,333 A | 9/1998 | Liprie |
| 5,851,172 A | 12/1998 | Bueche et al. |
| 5,910,101 A | 6/1999 | Andrew et al. |
| 6,048,300 A | 4/2000 | Thornton et al. |
| 6,061,588 A | 5/2000 | Thornton et al. |

FOREIGN PATENT DOCUMENTS

| | | |
|---|---|---|
| EP | 0 12 004 A | 6/1980 |

*Primary Examiner*—John P. Lacyk
(74) *Attorney, Agent, or Firm*—Cantor Colburn LLP

(57) ABSTRACT

There is provided a manually operable afterloader (100) for use during radiation therapy treatment of a patient. The afterloader (100) includes a sourcewire reel (112) having a circumferential groove, dual sized or stepped (188), for receipt of a non-radioactive portion of a sourcewire (130) and a shield capsule (154) having a passageway therethrough for receipt of a radioactive portion of a source wire (130). A cranking mechanism (163) is provided to rotate the sourcewire reel (112) and drive the radioactive sourcewire (130) out of the shield capsule (154).

15 Claims, 11 Drawing Sheets

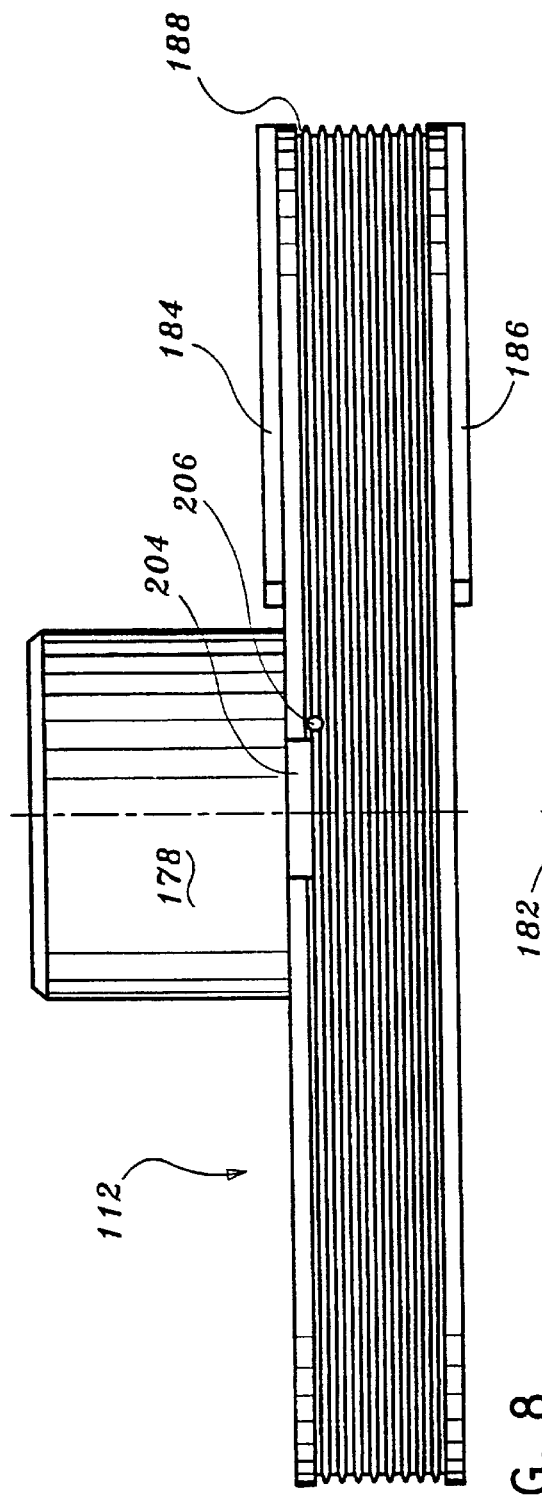
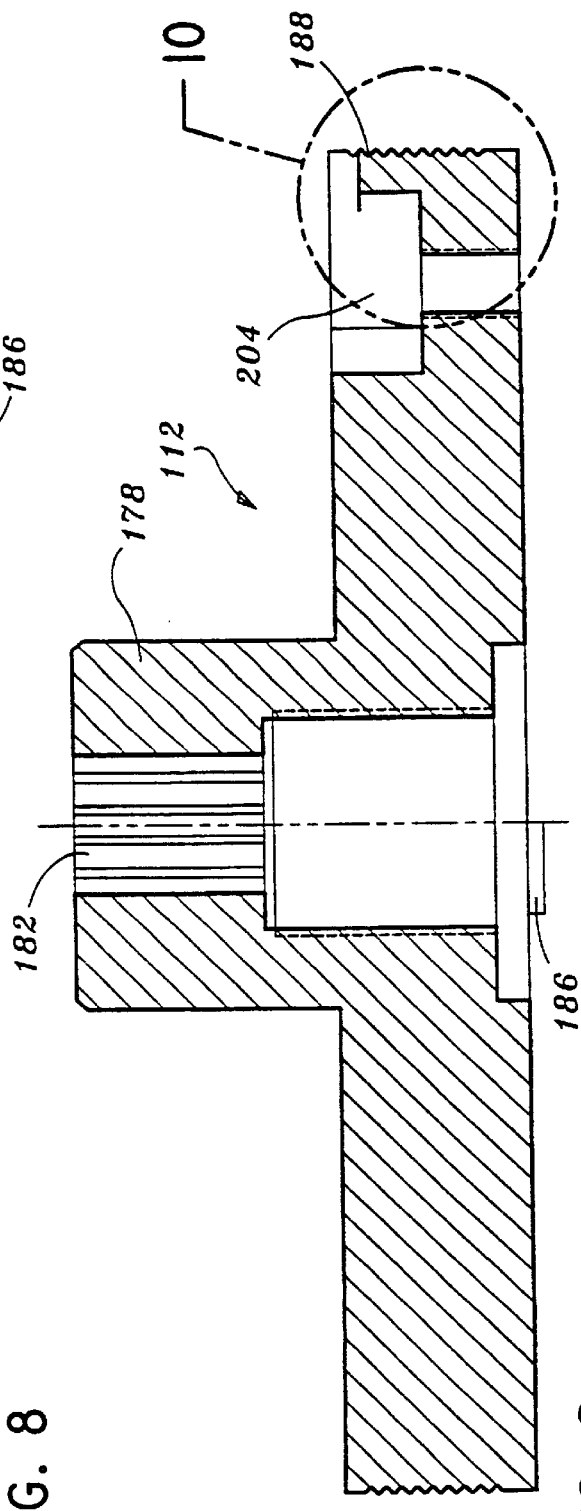
FIG. 8
FIG. 9

AFTERLOADER APPARATUS

CROSS REFERENCE TO RELATED APPLICATION

This application claims priority to U.S. Provisional Application Serial No. 60/059,602, filed Sep. 23, 1997, entitled, "Afterloader Apparatus".

BACKGROUND

1. Technical Field

The technical field relates generally to remote afterloading devices used to position radioactive treatment sourcewires within catheters inserted into patients to treat cancer or for use in conjunction with an angioplasty procedure, and, more particularly, to a manually operated afterloader.

2. Description of the Related Art

Radiation is used to treat cancer and other diseases of the body. Brachytherapy, is a general term for the radiation treatment of cancer at close distances inside the body. During brachytherapy, a radioactive source or sources are positioned in the area needing treatment. Angioplasty is a general term for opening a constriction in a blood vessel or artery. Radiation treatment has been found to be useful in preventing reclosure or restenosis of the constriction. Depending on the type of therapy, the radioactive sources are placed permanently inside the body during surgery, or transport tubes (treatment catheters) are placed in the body which are later temporarily loaded with radioactive sources via wires. This temporary afterloading of radioactive material involves a machine called an "afterloader" that will load and unload the radioactive material into and from the transport tubes.

Afterloaders are devices generally used accurately advance and retract a flexible drive member containing a radioactive source over a specified distance for a specified time period. An afterloader generally consists of a flexible simulation drive member, a flexible drive member containing a radioactive element or sourcewire, computer controllers and motorized drive mechanisms to operate both types of flexible members, a shielding safe for the radioactive element, an internal timer, and, in brachytherapy, an exit port attached to a rotating wheel that allows multiple transport tubes (previously placed into the patient) to be hooked up to the device at the same time. The afterloader usually sends out the simulation member to check the patency of the transport tube without subjecting the patient to undue radiation exposure, and then sends out the radioactive element. After the treatment is performed in the first transport tube, the afterloader retracts the source into the shielding safe inside the afterloader, a wheel turns and aligns a slot containing the second transport tube to an exit port. The afterloader then repeats its function sending and retracting the simulation member and radioactive member through this second tube. The procedure is repeated until the function is carried out through all the specified transport tubes. Since the afterloaders use a fixed, short length radioactive source, the afterloaders must multi-step this source many times inside each transport tube to cover the diseased area.

The current remote afterloaders on the market, initially designed for use in brachytherapy, are particularly complicated.

Limiting factors of prior art treatment afterloaders are the physical size and amount of equipment necessary to operate a remote afterloader. In many treatment facilities, there is not enough room for this amount and size of equipment.

When used with a sourcewire to treat a stenosis or constriction of an artery, an afterloader need not be so complex as to support multiple transport tubes or computer controlled indexing features.

Thus, there exists a need for a simple, compact, portable, self-contained afterloader for use in conjunction with, or after, an angioplasty procedure to provide radiation treatment of a vessel in order to prevent restenosis, i.e., reclosure.

SUMMARY

A manually operable afterloader is provided for use with a radioactive sourcewire having a relatively short radioactive portion and a relatively long nonradioactive portion. The afterloader generally includes a base plate having a sourcewire reel rotatably mounted thereon. The sourcewire reel includes a circumferential groove which is configured to receive the nonradioactive portion of the sourcewire. A shield capsule or safe is also mounted to the base plate and includes a passageway therethrough for receipt of the radioactive portion of the sourcewire. Preferably, the pathway through the shield capsule is nonlinear so as to prevent inadvertent escape of radiation from the capsule.

A guide tube is provided between the sourcewire reel and the pathway of the shield capsule. Adjustment structure or an adjustment clamp is provided about the guide tube to properly align one end of the guide tube with tangent of the sourcewire reel so as to receive the sourcewire from the reel.

The manually operable afterloader further includes a cranking mechanism which is operably engagable with the sourcewire reel. The cranking mechanism generally includes a crank wheel having a crank handle attached thereto. The crank wheel is connected to a drive shaft which in turn is connected to one side of a slip clutch. The sourcewire reel is mounted on a second shaft which is connected to the opposed side of the slip clutch. Thus, rotation of the crank wheel by a manipulation of the crank handle rotates the respective drive shafts through the clutch to drive the sourcewire on and off the sourcewire reel. Preferably, the slip clutch is designed to slip at a pressure of approximately two pounds to limit the driving or retraction forces provided to the sourcewire.

Further, as a safety mechanism, crank handle is pivotally mounted to the crank wheel such that when the crank handle is in a retracted position, it engages a mechanical or frictional safety thereby preventing inadvertent rotation of the crank wheel and thus the sourcewire reel. Further, a releasable braking mechanism may be provided to limit rotation of the sourcewire reel to an initial predetermined amount and, upon release of the braking mechanism, allow further rotation of the sourcewire reel.

The sourcewire reel includes a circumferential groove for receipt of the nonradioactive sourcewire and further includes a larger width or diameter groove above the sourcewire groove for receipt of a flexible cable or belt. The flexible belt is provided to restrain the sourcewire within the groove as the reel is rotated so that the sourcewire does not flex or pop out of the groove as it encounters resistive forces going to a treatment catheter. A takeup assembly is provided to control movement of the flexible cable and provide predetermined rates of tension on the cable so as to restrain the sourcewire within its respective groove. Preferably, the takeup assembly includes a first pulley fixedly mounted to the base and adjacent the sourcewire and a floating pulley floatingly mounted and biased by spring tension. An adjustment mechanism is provided to adjust the tension the flexible pulley provides about the belt relative to the fixed pulley.

BRIEF DESCRIPTION OF THE DRAWINGS

Various embodiments of the presently disclosed afterloader apparatus are described herein with reference to the drawing figures wherein:

FIG. 8 is an enlarged top view of the sourcewire reel;

FIG. 9 is a cross-sectional view of the sourcewire reel of FIG. 8 as rotated 90 degrees;

DETAILED DESCRIPTION OF PREFERRED EMBODIMENTS

Figure 1:
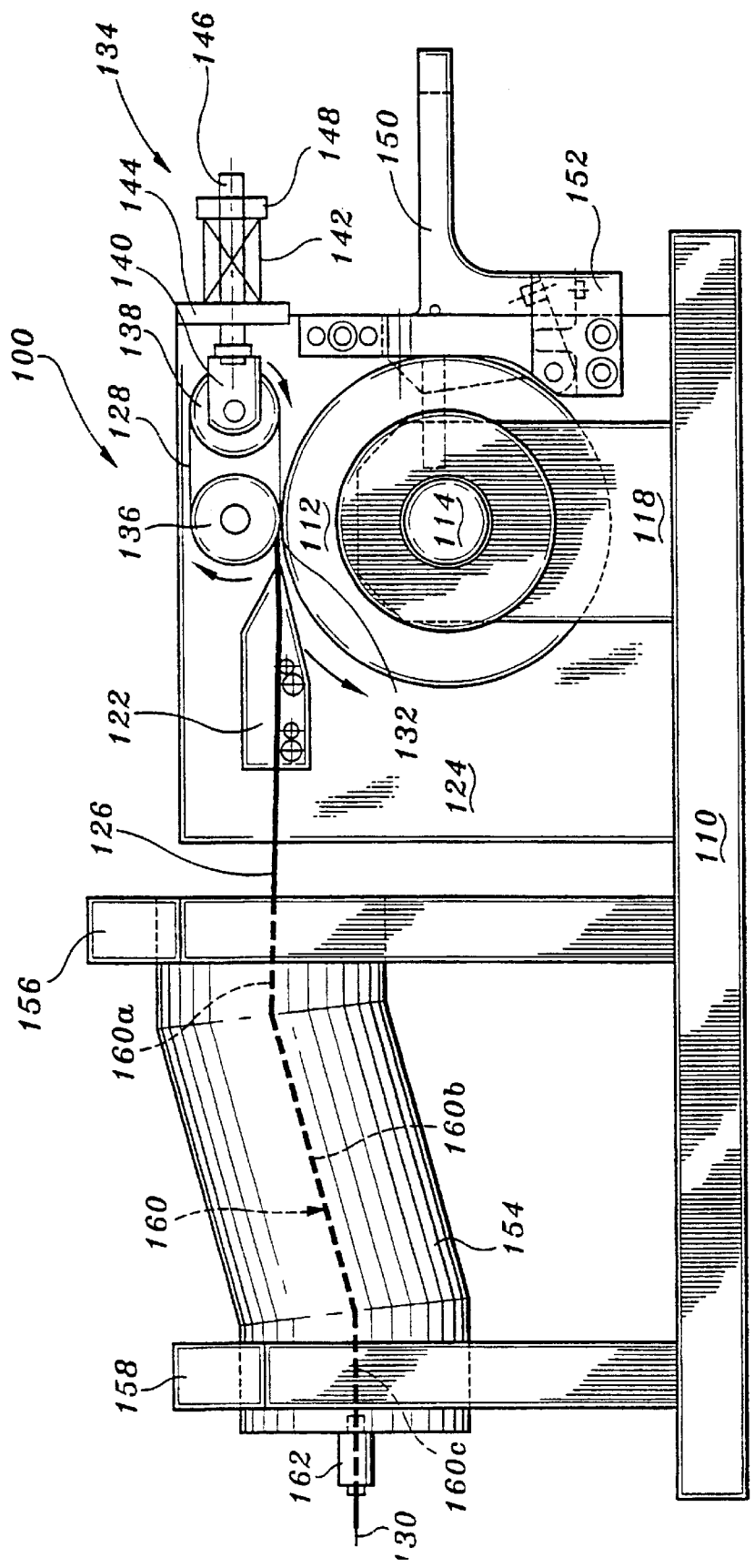
FIG. 1 is a side view of an afterloader apparatus constructed in accordance with a first embodiment of the present disclosure.

Referring now in detail to the drawing figures in which like reference numerals identify similar or identical elements, a first embodiment of the afterloader apparatus of the present disclosure is illustrated in FIGS. 1–11, and is designated generally by the reference numeral 100. Briefly, the general function of afterloader 100 is to deliver a sourcewire having a radioactive source contained near a distal end to a treatment site within a vessel of a patient to prevent the restenosis of the vessel after an angioplasty procedure. Afterloader 100 drives the sourcewire through a treatment catheter which is attached to afterloader 100 and extends to the treatment site within the vessel. The frame components of afterloader 100 are made of tool grade aluminum or steel. The materials utilized for the various other components of afterloader 100 will be identified as appropriate.

Figure 2:
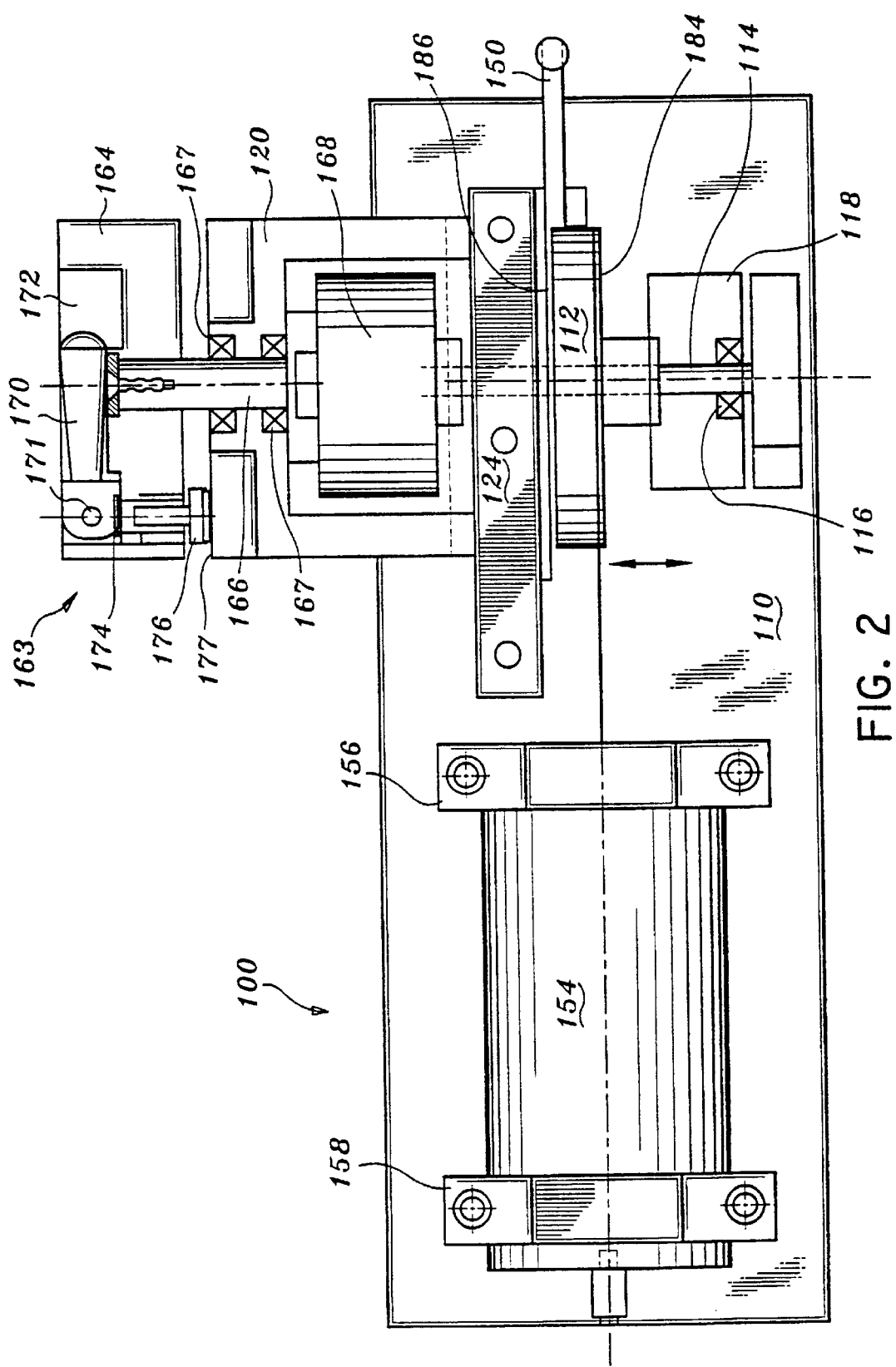
FIG. 2 is a top view of the afterloader apparatus embodiment of FIG. 1.
Figure 3:
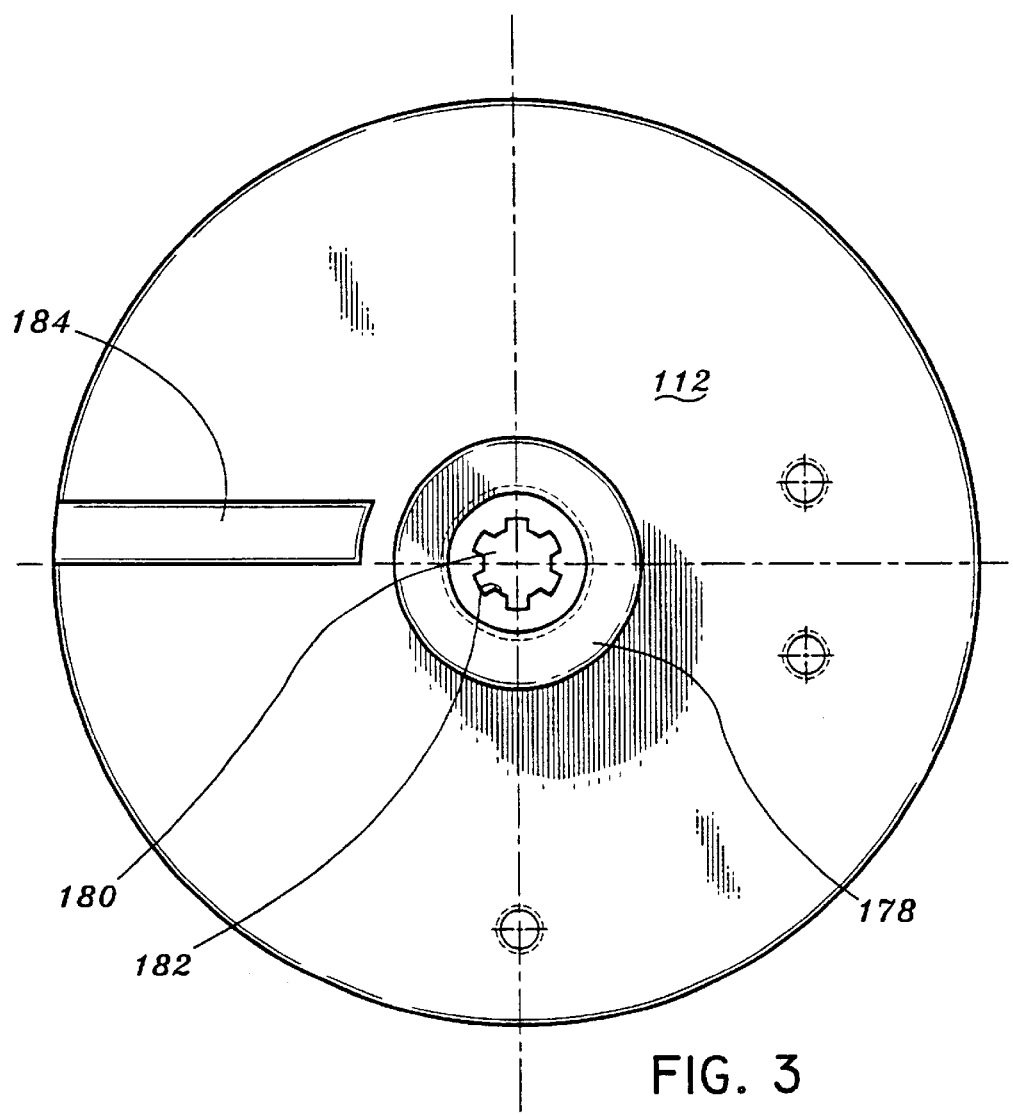
FIG. 3 is a side view of the sourcewire reel of the afterloader apparatus.

Referring initially to FIGS. 1 and 2, afterloader 100 includes a frame base plate 110 having a sourcewire reel 112 rotatably disposed thereabove by a shaft 114 which is supported by a roller bearing 116 mounted in vertical support frame 118. Additional bearings which support a drive shaft for rotatable motion will be described further herein.

A guide tube clamp 122 is secured to a vertically oriented mounting plate 124 which in turn is secured to base plate 110. A guide tube 126 is aligned with a tangent of sourcewire reel 112 and defines the path along which a sourcewire 130 is payed out from sourcewire reel 112. Guide tube clamp 122 is adjustable to align an end of guide tube 126 with sourcewire 130 retained on sourcewire reel 112. The components of guide tube clamp 122 are thereafter tightened to fix the alignment of guide tube 126 relative to the sourcewire path.

A cable or flexible belt 128 is provided to securely retain a flexible sourcewire 130 on sourcewire reel 112. In order to payout sourcewire 130 from sourcewire reel 112, a tangent opening 132 is provided by a take-up assembly 134 which serves to divert flexible belt 128 from sourcewire reel 112 temporarily to allow a gap to be formed at tangent opening 132 thus permitting sourcewire 130 to exit sourcewire reel 112 tangentially and enter guide tube 126 which, as noted above, is adjusted to have an opening aligned with the tangent coming off of tangent opening 132.

An adjustable take-up assembly 134 is provided to guide and tension flexible belt 128. Takeup assembly 134 includes a fixed pulley 136 rotatably secured to mounting plate 124 and a floating pulley 138 which is rotatably mounted by way of a yoke 140 through a bracket 144. A first end of flexible belt 128 is secured to sourcewire reel 112 with a clamp (described below). Belt 128 is wound over sourcewire 130, and is deflected away from sourcewire 130 and onto fixed pulley 136, around floater pulley 138 and back to a second clamp on sourcewire reel 112. Takeup assembly 134 also includes a threaded adjusting rod 146 and nut 148. Threaded adjusting rod 146 is connected to yoke 140. A compression spring 142 is disposed between nut 148 and bracket 144 to spring bias threaded rod 146 and hold it and floating pulley 13 tension thereby tensioning flexible belt 128. The tension of flexible belt 128 can be adjusted by advancing or retracting nut 148 on thread rod 146 to achieve the desired tension.

A releasable brake mechanism or stop release lever 150 is pivotally mounted to a bracket 152 which is secured to mounting plate 124. Stop release lever 150 is preferably spring biased toward an engaged orientation with sourcewire reel 112. The stop release lever 150 limits rotation of sourcewire reel 112 to a predetermined initial amount so that sourcewire 130 can initially only advance a predetermined distance. The predetermined distance is preferably chosen to allow a distal end of sourcewire 130 to advance to within about 3–5 cm of the distal end of a blind lumen in an associated treatment catheter. This prevents sourcewire 130 from hitting or piercing the distal end of the blind lumen and allows, when the braking mechanism is released, fine tuning of the position of the radioactive source, on the distal end of the sourcewire, within the treatment zone of the catheter. This may be accomplished with the aid of fluoroscopy. Stop release lever 150, is pivoted to a disengage position disconnecting it from sourcewire reel 112 to allow a further limited amount of advancement of sourcewire 130.

A shield capsule 154 is securely disposed above frame base plate 110 by proximal vertical support 156 and distal vertical support 158. Shield capsule 154 is preferably formed of a material which prevents the escape of radiation from a radioactive source. To accomplish the prevention of escape of the radiation, which can only travel in smear or line of sight direction, from a !active source contained at the distal end of sourcewire 130, shield capsule 154 defines a pathway 160 which is non-linear. In particular, pathway 160 includes linear segments 160a, 160b and 160c which are in communication to form a continuous non-linear pathway 160 through shield capsule 154. When the radioactive source is positioned at the mid-point of shield capsule 154, radiation is prevented from escaping out the open ends of pathway 160 due to the non-linear configuration of pathway 160 preventing the emission of radiation therefrom which, as noted above, travels in a line of sight capacity only. While interconnected linear segments are disclosed to form pathway 160, it is contemplated that other non-linear configurations, such as, for example, curvilinear, may be used as long as the pathway allows unimpeded travel of sourcewire 130 therethrough. At the outlet of pathway 160 a connector member such as Luer connector 162 is provided in order to connect guide tube 126 with a treatment catheter (not shown). Preferably connector 162 is a proprietary type connector configured to mate only with a correspondingly configured connector on a treatment catheter or extension tube.

Referring to FIG. 2, to facilitate payout of sourcewire 130 from sourcewire reel 124, a cranking mechanism 163 is provided which includes a crank wheel 164 securely mounted to a drive shaft 166 which in turn is operatively connected to a clutch 168. Drive shaft 166 is rotatably mounted with respect to base plate 110. Clutch 168 may be any suitable slip clutch type, for example, a Berg model no. JCO-4 is one suitable clutch which acts as a slip clutch in one direction. An opposite side of clutch 168 is connected to sourcewire reel 124 by way of shaft 114. Clutch 168 is preferably rated to slip at approximately two pounds of force to limit the drive and retraction forces provided to sourcewire 130. This is desirable to prevent sourcewire 130 from advancing through the walls of a treatment catheter and to prevent retraction of sourcewire 130 if stuck within the treatment catheter. Preferably, a two-way clutch may be utilized to provide the user with a positive indication at the extreme limits of travel for sourcewire 130. Drive shaft 166 is supported by bearings 167 in support frame 120.

A crank handle 170 is preferably pivotally attached to crank wheel 164 by a pivot pin 171 and is movable between a retracted position, as shown in FIG. 2, wherein crank handle 170 in a recess 172 formed in crank wheel 164 and a operative position wherein crank handle 170 is rotated 90 degrees outwardly from its retracted position. A curved camming surface 174 is provided on crank handle 170 to interact with a stop member 176 which is preferably spring loaded to be biased in a retracted orientation such that when crank handle 170 is in the operative position, stop member 176 is biased away from housing wall 177. Stop member 176 is biased against housing wall 177 by the outer surface of crank handle 170 when crank handle 170 is in the retracted position as illustrated in FIG. 2. In this manner, stop member 176 frictionally engages housing wall 177 to prevent inadvertent operation of crank wheel 164. Preferably top member 176 is formed from a material having a high coefficient of friction.

Figure 4:
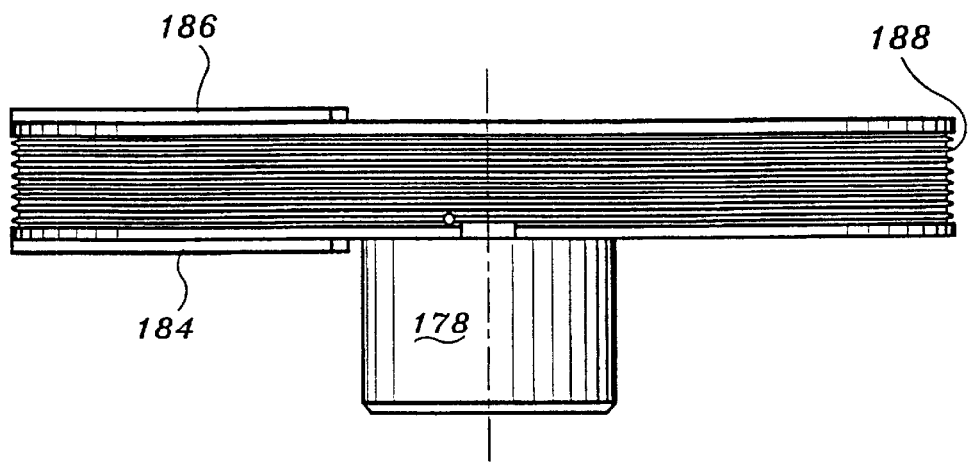
FIG. 4 is a top view of the sourcewire reel of FIG. 3.

Referring now to FIGS. 3–10, specific details of a preferred embodiment of sourcewire reel 112 will now be addressed in greater detail. Sourcewire reel 112 includes a cylindrical hub 178 which surrounds a mounting bore 180. Mounting bore 180 is configured and dimensioned to securely receive shaft 114. Preferably, bore 180 is provided with gear teeth 182 which mesh with complimentary gear teeth formed on shaft 114 to ensure that no slippage occurs between sourcewire reel 112 and shaft 114. A pair of stop members 184 and 186 are provided on the outer surfaces of sourcewire reel 112. Stop members 184 and 186 prevent sourcewire reel 112 from being rotated so far that sourcewire 130 detaches from sourcewire reel 112. Stop member 184 limits the amount of rotation of sourcewire reel 112 in a first direction, and thus the distance sourcewire 130 travels in a first direction. Stop member 186 similarly limits the amount of rotation of sourcewire reel 112 in a second direction and thus limits the distance sourcewire 130 travels in a second direction. Finally, as shown in FIG. 4, a threaded groove 188 is formed around the outer perimeter of sourcewire reel 112. Threaded groove 188 receives both the sourcewire 130 and flexible belt 128.

Figure 6:
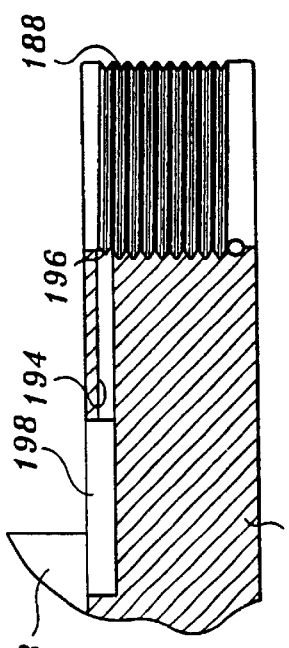
FIG. 6 is a cross-sectional view taken along section line 6—6 of FIG. 5.
Figure 7:
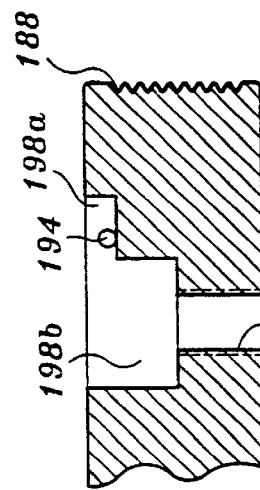
FIG. 7 is a cross-sectional view taken along section line 7—7 of FIG. 5.
Figure 5:
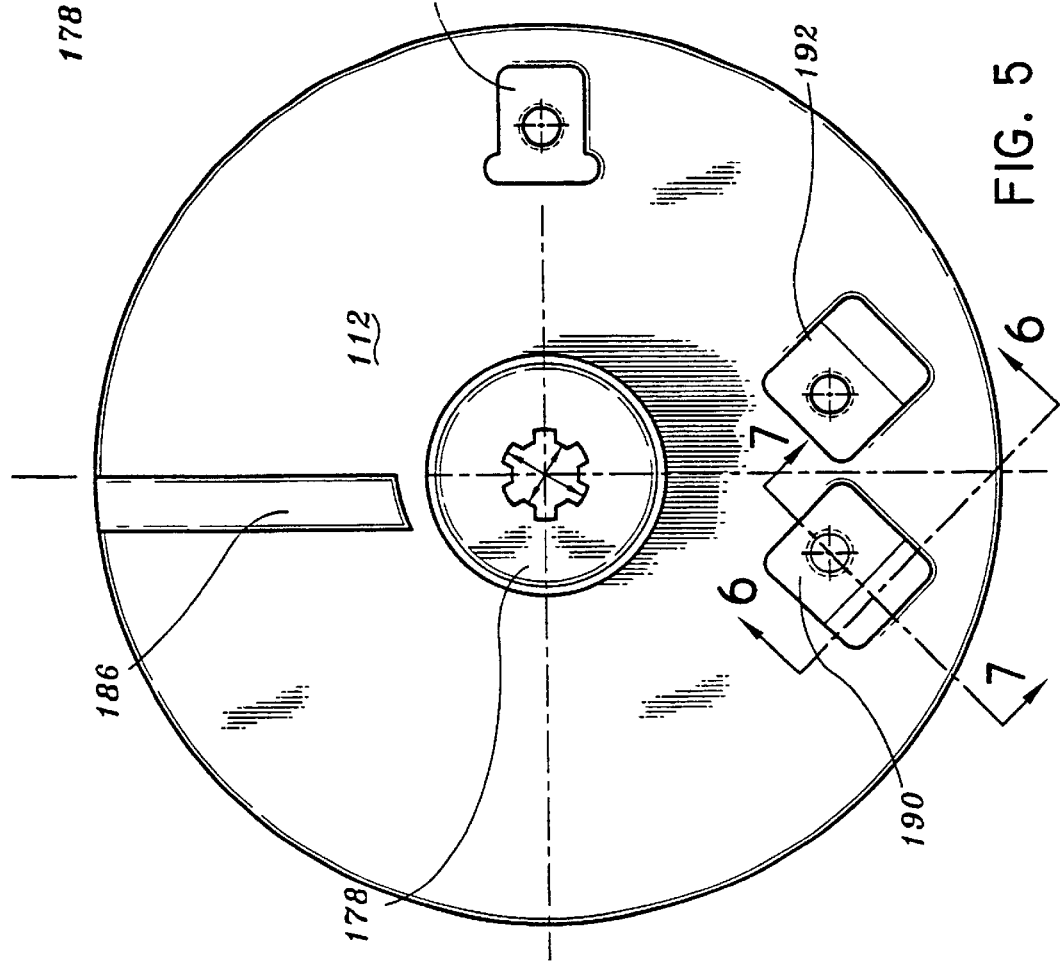
FIG. 5 is a side view of the sourcewire reel illustrating the side opposite to that illustrated in FIG. 3.

Referring now to FIG. 5, in order to retain a first or proximal most ends of the sourcewire 130 and flexible belt 128, a pair of clamps 190 and 192 may be provided on sourcewire reel 112. The operation of clamps 190 and 192 will be explained with reference to FIGS. 5–7 which show the details of clamp 190. Clamp 192 operates in the same manner. As shown in FIG. 6, sourcewire reel 112 is provided with a bore 194 formed to extend from terminus 196 of threaded groove 188 to a recess 198 formed in the surface of sourcewire reel 112 a radial distance inwardly from the outer edge of the sourcewire reel. In this manner, the sourcewire 130 or flexible belt 128 as appropriate, is fed through bore 194 into recess 198. Thereafter, clamp 190 is threadably secured into recess 198 to secure a respective end of sourcewire 130 or belt 128 within recess 198. As shown in FIG. 7, recess 198 is preferably formed as a stepped recess having an upper shelf portion 198a and a lower shelf portion 198b. A threaded bore 200 is provided in communication with lower shelf portion 198b. Clamp 190 is preferably configured and dimensioned to the same configuration of recess 198 with slightly smaller dimensions in order to fit therein. Clamp 190 is secured in recess 198 by a threaded screw (not shown).

Referring to FIG. 5, a transport clamp 202 is provided to retain the outer end of flexible belt 128 during transport of sourcewire reel 112. This is necessary to replace the sourcewire on afterloader 100 with a new sourcewire depending upon the level of radioactivity and decay of the sourcewire. Referring to FIGS. 8 and 9, clamp 202 fits within a recess 204 formed in sourcewire reel 112. Clamp 202 functions in a similar manner as clamps 190 and 192. For example, a bore 206 FIG. 8 is formed radially inward through sourcewire reel 112 at the beginning of threaded groove 188. Bore 206 is in communication with recess 204 so that clamp 202 may secure the end of flexible belt 128 therein.

Figure 10:
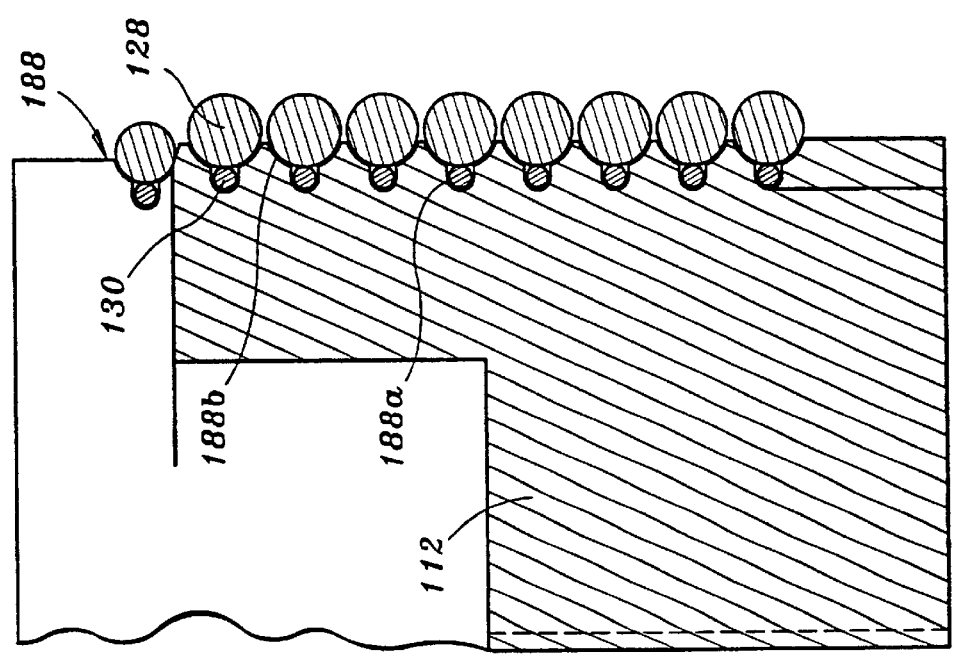
FIG. 10 is an enlarged view of the indicated area of detail shown in FIG. 9, which shows the threaded groove configuration.

Referring to FIG. 10, the wrapping arrangment of flexible belt 128 around sourcewire reel 112 to retain sourcewire 130 within threaded groove 188 will now described in detail. Threaded groove 188 is preferably formed as a compound groove 188 having a lower groove portion 188a formed directly radially inwardly of outer groove portion 188b. Sourcewire 130 is wrapped onto sourcewire reel 112 within threaded groove portion 188a and flexible belt 128 is wrapped around sourcewire reel 112 over sourcewire 130 and is retained in outer groove portion 188b. As illustrated in FIG. 10, the diameter of flexible belt 128 is significantly larger than that of sourcewire 130. In this manner, flexible belt 128, upon paying out of sourcewire 130 from sourcewire reel 112, prevents resistant forces, which are created due to negotiation of sourcewire 130 through the catheter and numerous turns through a tortuous passageway to the treatment site, from forcing sourcewire 130 out of threaded groove 188.

Figure 11:
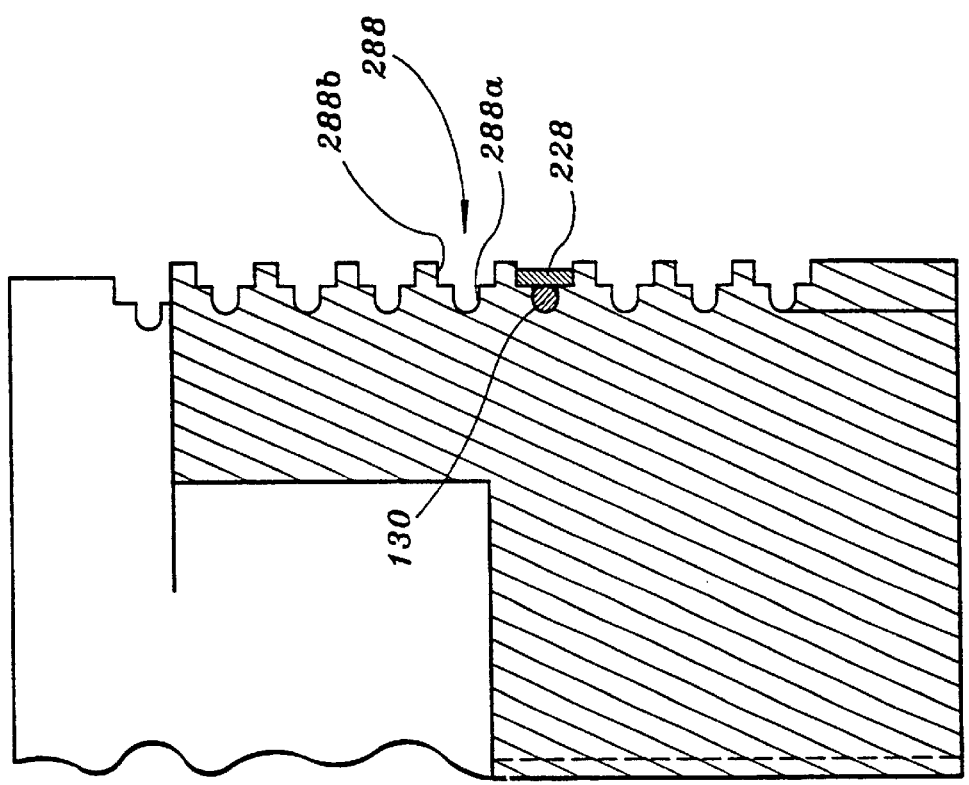
FIG. 11 is an alternative embodiment of the threaded groove configuration of FIG. 10.

Referring to FIG. 11, an alternative embodiment of retaining sourcewire 130 within sourcewire reel 112 is illustrated by threaded groove 288 which includes a arcuate lower portion 288a and a squared-off upper portion 288b. Sourcewire 130 is retained in lower portion 288a by flexible belt 228 having a rectangular cross-section. It is within the scope of the present disclosure that numerous different geometries may be utilized for the groove portions as well as flexible belt 228.

Figure 12:
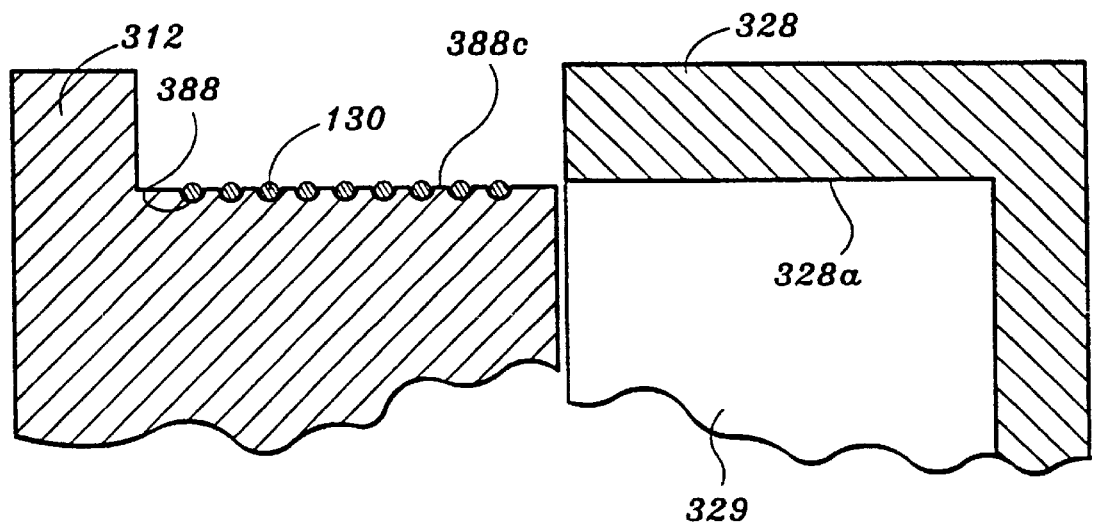
FIG. 12 is a partial cross-sectional view of an alternative embodiment for retaining the sourcewire on the sourcewire reel.
Figure 13:
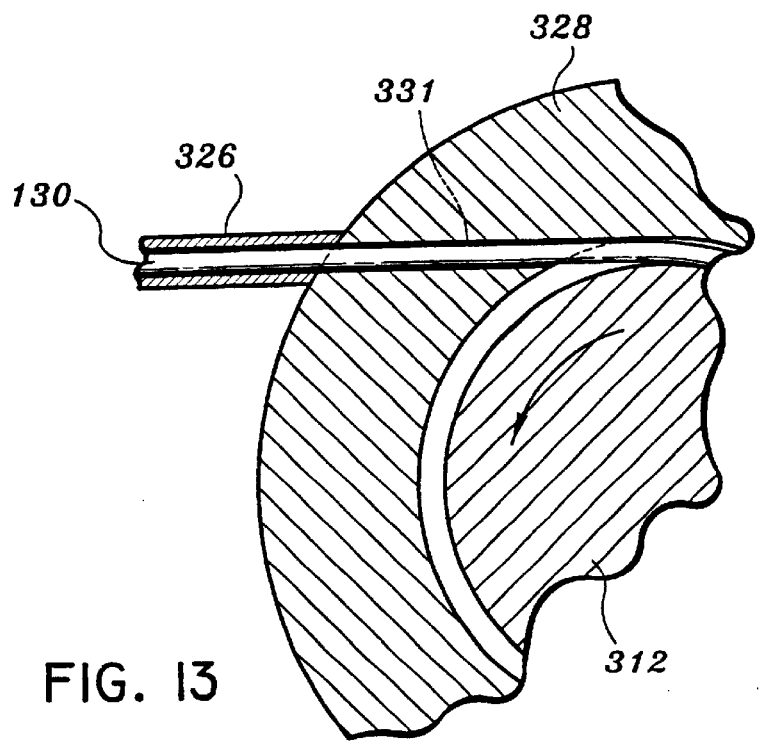
FIG. 13 is a partial cross-sectional view illustrating the payout passageway of the sourcewire from the sourcewire reel according to the alternative embodiment of FIG. 12.
Figure 14:
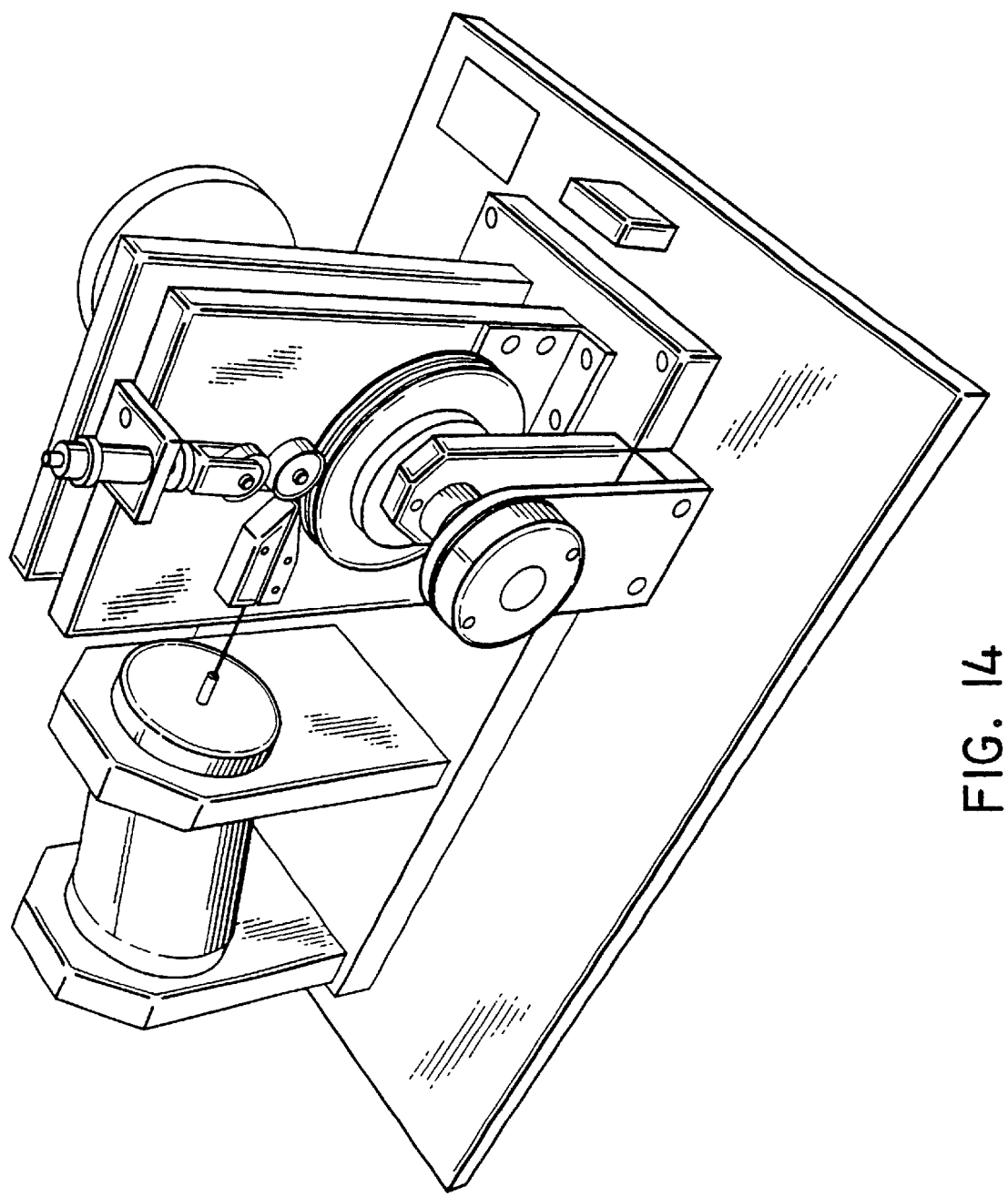
FIG. 14 is perspective view of an alternative afterloader apparatus embodiment constructed substantially in accordance with the present disclosure.
Figure 15:
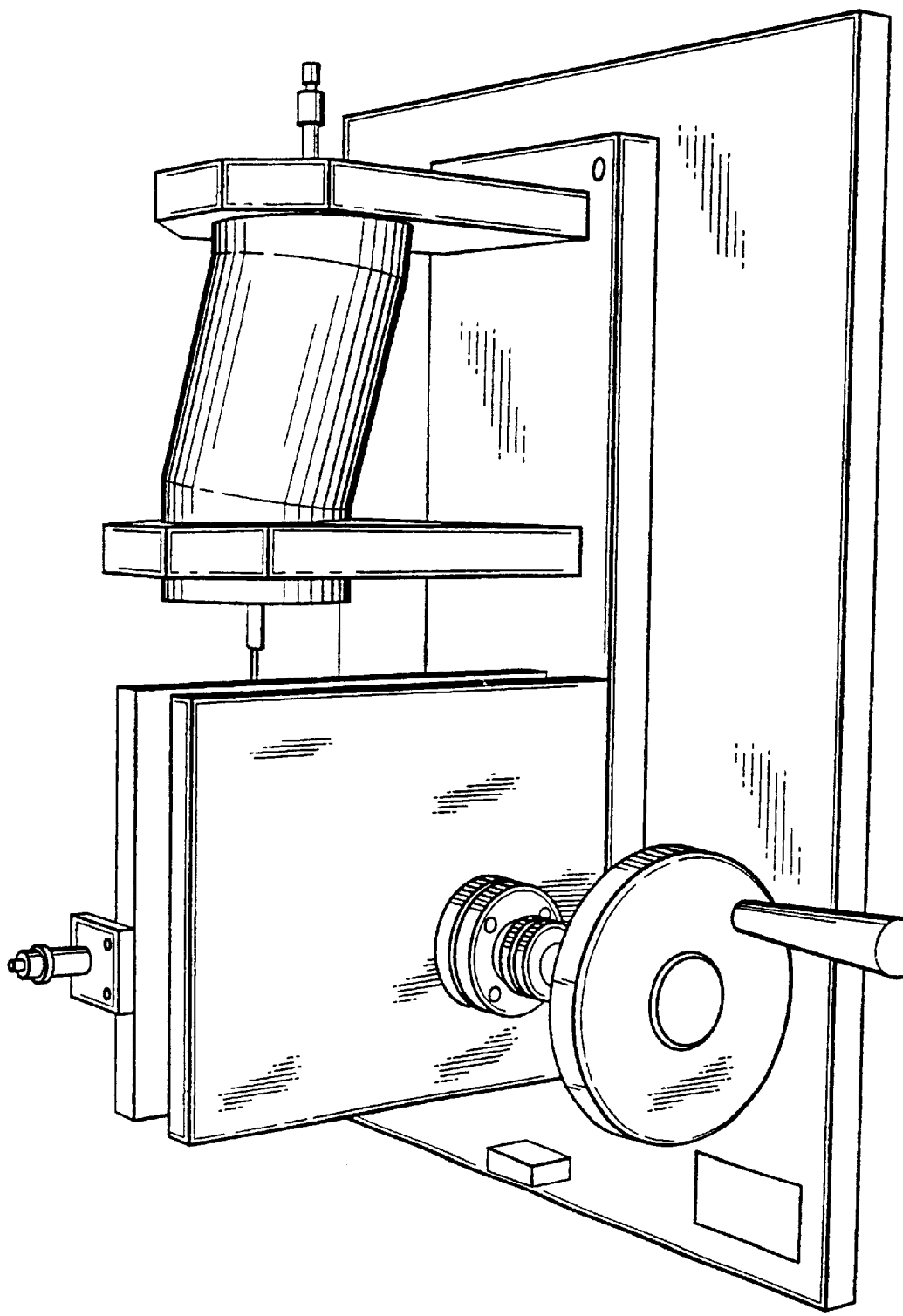
FIG. 15 is a side perspective view of the afterloader apparatus embodiment of FIG. 14.
Figure 16:
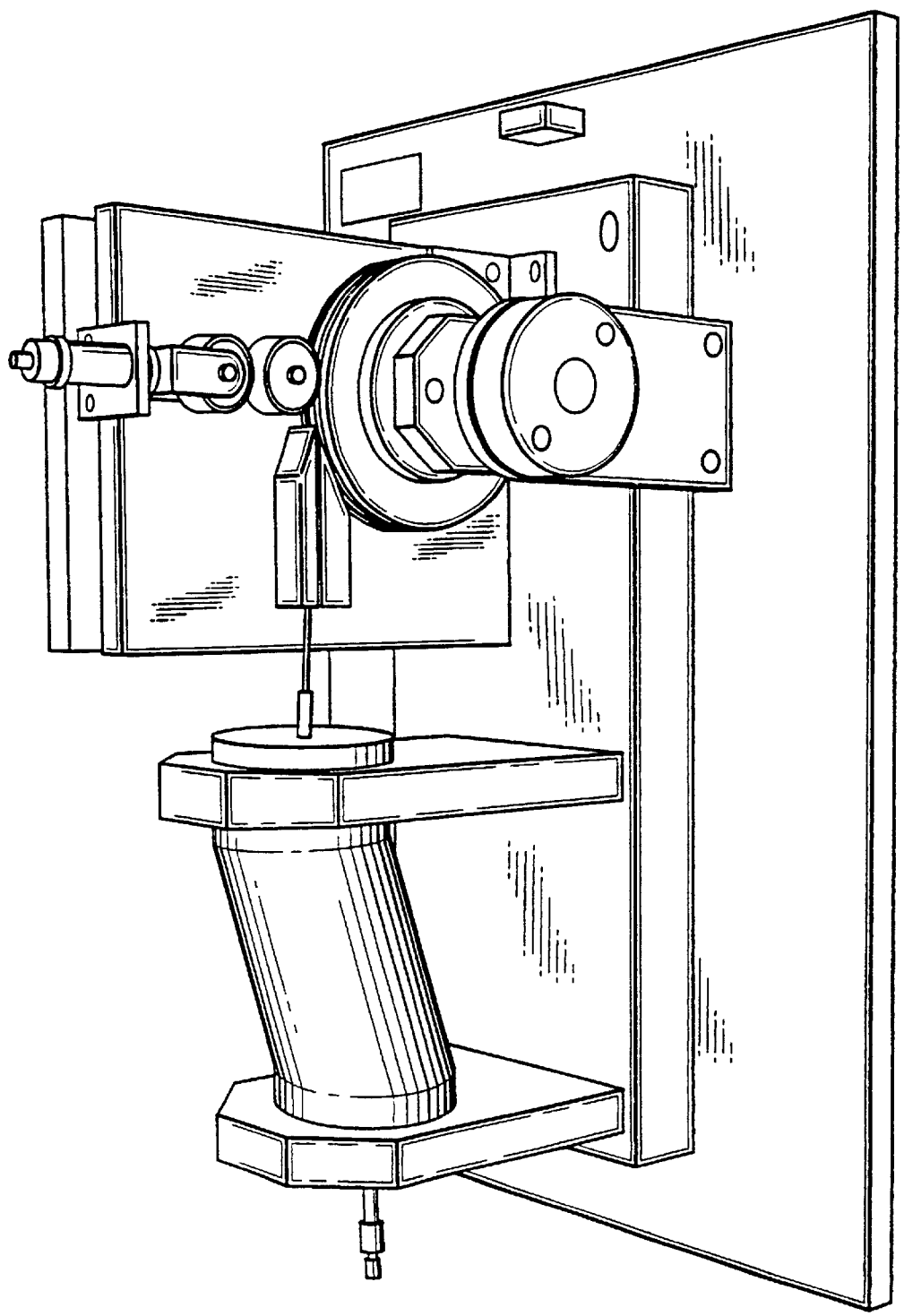
FIG. 16 is a side perspective view from the side opposite that illustrated in FIG. 15.
Figure 17:
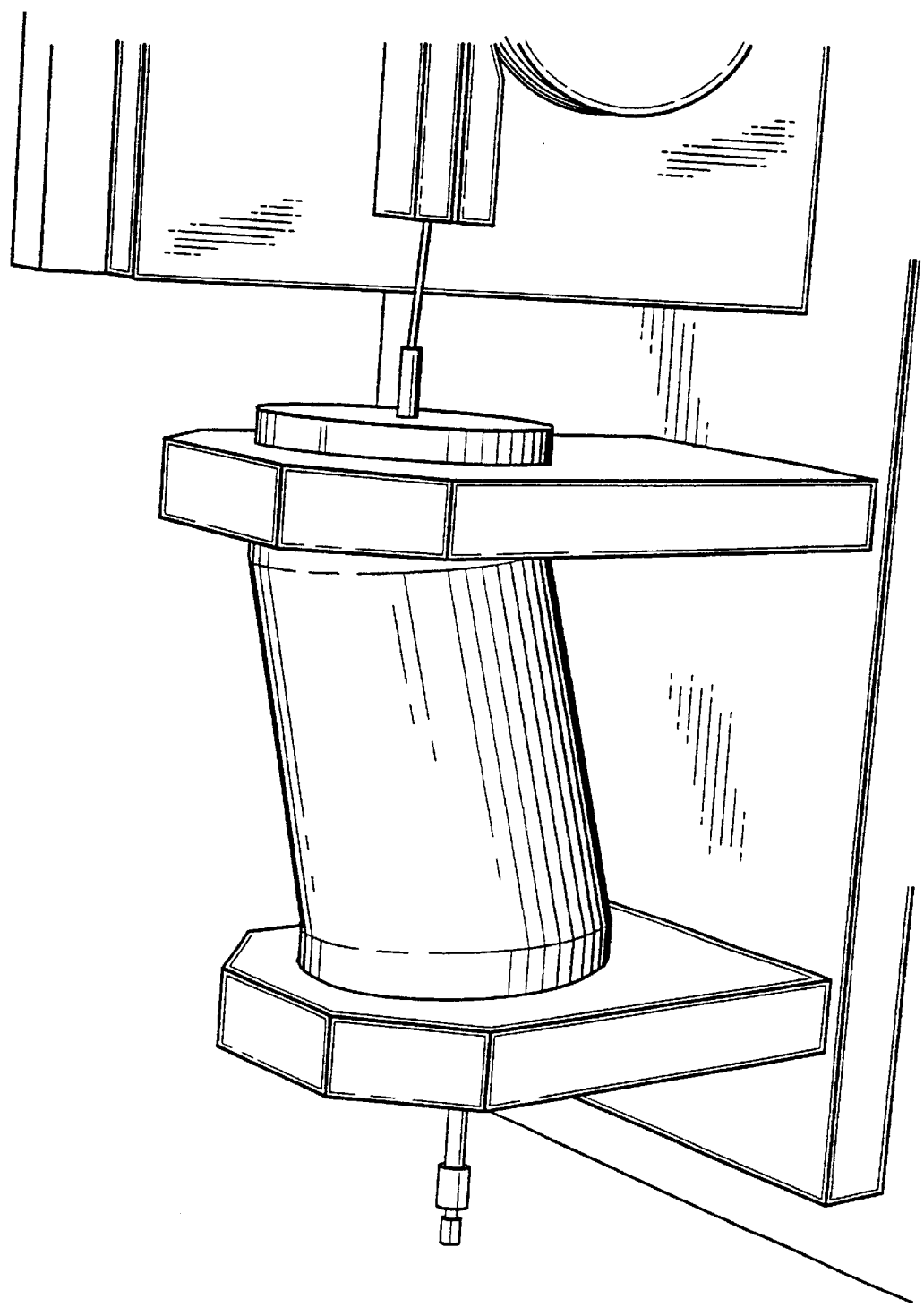
FIG. 17 is an enlarged perspective view of the shield capsule of the afterloader apparatus.

Referring to FIGS. 12 and 13, a further alternative embodiment for retaining sourcewire 130 within a threaded groove 388 of a sourcewire reel 312 is illustrated. Souceewire reel 312 is similar to sourcewire r 112 except that the configuration is modified to accommodate a retaining cover 328 which is formed as a cylindrical member having a cylindrical recess 329 formed therein. Retaining member 328 performs a similar function to that of flexible belt 128 above and acts as a cap which is inserted over sourcewire reel 312 to retain sourcewire 130 in threaded groove 388.

Retainer member 328 is configured and dimensioned such that the inner side wall surface 328a forms a cylindrical sidewall having a diameter slightly larger than the diameter of the ridges 388c of threaded groove 388. In this manner, upon insertion of retainer 328 over threaded groove 388, sourcewire 130 is slightly impinged against threaded groove 388 and is thereby prevented from leaving threaded groove 388.

A bore 331 is formed through retainer 328 in tangential relationship with threaded groove 388. In this manner, sourcewire 130 is permitted to payout or exit threaded groove 388 upon rotation of sourcewire 312 as indicated by the arrow in FIG. 13. Sourcewire 130 enters into guide tube 326 having an inlet opening in communication with bore 331 so as to receive source wire 130.

Referring now to FIGS. 14–17, an alternative embodiment of an afterloader apparatus is depicted in the digital images shown therein. The afterloader illustrated in FIGS. 14–17 is substantially the same in structure and operation as afterloader 100 described hereinabove. One difference between the afterloader depicted in FIGS. 14–17 and afterloader 100 is shown in 15 wherein the crank handle is fixed in a operable position to permit cranking of the crank wheel at all times. A further difference is that the takeup assembly is oriented vertically rather than horizontally, as is takeup assembly 134 of afterloader 100. Other minor differences may be provided without affecting the overall functioning and sourcewire retaining structure of the disclosed manually operated afterloader.

Although the illustrative embodiments of the present disclosure have been described herein with reference to the accompanying drawings, it is to be understood that the disclosure is not limited to those precise embodiments, and that various other changes and modifications may be affected therein by one skilled in the art without departing from the scope or spirit of the disclosure. All such changes and modifications are intended to be included within the scope of the present disclosure.

What is claimed is:

1. A manually operated afterloader for use with a radioactive tipped elongated sourcewire, the sourcewire having a relatively short radioactive portion and a relatively long non-radioactive portion comprising:
    a base;
    a shield capsule defining a pathway therethrough for receipt of a radioactive portion of a sourcewire;
    a sourcewire reel rotatably mounted with respect to the base, the sourcewire reel having a threaded groove formed in the circumference thereof for receipt of a non-radioactive portion of a sourcewire;
    a manually operable cranking mechanism mounted to the base and engagable with the sourcewire reel to rotate the sourcewire reel, the cranking mechanism, when operated driving the non-radioactive portion of the sourcewire out of the threaded groove to drive the radioactive portion of the sourcewire through the pathway and out of the shield capsule.

2. The manually operated afterloader as recited in claim 1, further comprising a flexible belt mounted for engagement with the sourcewire reel such that the flexible belt biases the non-radioactive portion of the sourcewire within the threaded groove.

3. The manually operated afterloader as recited in claim 2, wherein the flexible belt is mounted around a first pulley biasing a portion of the flexible belt into engagement with the sourcewire reel and a second pulley tensioning the flexible belt.

4. The manually operated afterloader as recited in claim 3, wherein the first pulley is fixed relative to the base plate and the second pulley is movable relative to the base plate so as to tension the flexible belt between the first and second pulleys.

5. The manually operated afterloader as recited in claim 4, wherein the second pulley is mounted on a spring biased yoke movably mounted with respect to the base plate.

6. The manually operated afterloader as recited in claim 1, wherein the threaded groove is a compound groove having a first portion dimensioned to receive the non-radioactive portion of the source wire and a second portion dimensioned to receive the flexible belt, the first portion being located radially inwardly of the second portion.

7. The manually operated afterloader as recited in claim 6, wherein the first portion has a first diameter and the second portion has a second diameter greater than that of the first portion.

8. The manually operated afterloader as recited in claim 6, wherein the second portion of the threaded groove has a substantially rectangular cross-section.

9. The manually operated afterloader as recited in claim 1, further comprising a guide tube positioned between the sourcewire reel and the shield capsule such that one end of the guide tube is aligned with a tangent of the sourcewire reel and an opposite end of the guide tube is aligned with one end of the pathway through the shield capsule.

10. The manually operated afterloader as recited in claim 9, further comprising an adjustable guide tube clamp mounted relative to the base plate and engagable with the guide tube to align the guide tube with a tangent of the sourcewire reel.

11. The manually operated afterloader as recited in claim 1, wherein the pathway is non-linear.

12. The manually operated afterloader as recited in claim 1, wherein the cranking mechanism includes a drive shaft rotatably mounted with respect to the base plate, a crankwheel affixed to one end of the drive shaft and a slip clutch operatively connected to the other end of the drive shaft, the slip clutch being connected to the sourcewire reel.

13. The manually operated afterloader as recited in claim 12, wherein the cranking mechanism further includes a crank handle movable between a first position allowing rotation of the drive shaft and a second position frictionally restraining the drive shaft from being rotated.

14. The manually operated afterloader as recited in claim 1, further comprising a releasable braking mechanism engagable with the sourcewire reel, the braking mechanisms halting rotation of the sourcewire reel after a predetermined amount of rotation of the sourcewire reel.

15. The manually operated afterloader as recited in claim 1, wherein the sourcewire reel includes a first stop block limiting the amount of rotation of the the sourcewire reel in a first direction and a second stop block limiting the amount of rotation of the sourcewire reel in a second direction.

* * * * *